United States Patent [19]

Faybishenko

[11] Patent Number: 5,941,121

[45] Date of Patent: Aug. 24, 1999

[54] TENSIOMETER FOR SHALLOW OR DEEP MEASUREMENTS INCLUDING VADOSE ZONE AND AQUIFERS

[75] Inventor: Boris Faybishenko, Berkeley, Calif.

[73] Assignee: The Regents of the University of California, Oakland, Calif.

[21] Appl. No.: 08/843,000

[22] Filed: Apr. 17, 1997

[51] Int. Cl.$^6$ ........................................................ G01L 5/02
[52] U.S. Cl. ........................................................ 73/73
[58] Field of Search .............................. 73/73; 137/78.3, 137/624.11; 239/63.64, 69, 70

[56] References Cited

U.S. PATENT DOCUMENTS 4,548,225  10/1985  Busalacchi .............................. 137/78.3
4,922,945   5/1990  Browne ....................................... 73/73

*Primary Examiner*—William Oen
*Attorney, Agent, or Firm*—Coudert Brothers

[57] ABSTRACT

A two cell tensiometer is described in which water level in the lower cell is maintained at a relatively constant height, and in equilibrium with the water pressure of materials that surround the tensiometer. An isolated volume of air in the lower cell changes pressure proportionately to the changing water pressure of the materials that surround the tensiometer. The air pressure is measured remotely. The tensiometer can be used in drying as well as wetting cycles above and below the water table.

23 Claims, 8 Drawing Sheets

TENSIOMETER FOR SHALLOW OR DEEP MEASUREMENTS INCLUDING VADOSE ZONE AND AQUIFERS

This invention was made with U.S. Government support under Contract No. DE-AC03-76SF00098 between the U.S. Department of Energy and the University of California for the operation of Lawrence Berkeley National Laboratory. The U.S. Government may have certain rights in this invention.

BACKGROUND OF THE INVENTION

1. Field of the Invention

This invention relates generally to tensiometers and more specifically to deep direct measurement of water pressure, moisture content, and water flux.

2. Description of Related Art

Water migration in shallow soils and rocks have been measured using tensiometers with water-filled tubes. This type of tensiometer is not useful at depths greater than about 7 meters below the soil surface because the water level in the measurement tube varies in a manner that cannot be known by the person at the surface taking the measurement as described by Daniel B. Stephens on pages 204 to 207 of his text, Vadose Zone Hydrology, (Lewis Publishers: Boca Raton, Fla. 1996).

In 1977 Dzekunov and Faybishenko (Device for determination of water pressure in soils (title translated from Russian), Certificate of Invention No. 591761, Moscow, 1977) designed a tensiometer having a porous ceramic wall at the bottom and an inverted solid cup some distance up from the ceramic bottom. This work is also described in a text by Faybishenko, entitled Water-Salt Regime of Soils under Irrigation (title translated from Russian), Moscow, Agropromisdat, 1986. The tensiometer was filled with water in a manner that left air trapped under the inverted solid cup. The lower porous wall allowed the water inside the tensiometer to come to equilibrium with the water in the surrounding soil. A second air space was left at the upper end of the tensiometer and the vapor pressure was measured to verify that the upper cell had not drained all its water. In the lower cell, when water leached out of the ceramic wall due to soil drying, the lower cell air pressure changed proportionately. Only two tubes extended from the tensiometer to the soil surface. One extended from the air phase in the upper cell and one from the air phase in the lower cell. The upper cell tube was used to replenish water and allow air to escape so that the pressure would not increase and force water into the tube that connected to the air volume in the lower cell. If that happened, the pressure measurement in the lower chamber was affected by the amount of the weight of water that entered the tube, and errors arose. The lower cell tube was used to measure lower cell air pressure. There were two major difficulties with this design. The first is that measurement of lower cell air pressure had to stop during the time upper-cell water was being replenished. In addition, the water had to be refilled very slowly and with very little control, so water was frequently forced into the lower cell air-pressure measurement tube. Secondly, in this design, the volume of air in the tube that extended from the lower-cell air pocket to the surface was too large for an effective instrument. The volume of air in the tube connecting the pressure sensor to the lower cell almost equaled the air in the confined volume of the lower cell. The result was a slow response time to pressure changes in the surrounding water, loss in sensitivity of measurement, and water column variations in the lower cell water column that sometimes became so great as to wash into the air pressure measurement tube.

Villa Nova et al. (Soil Technology, 2:403–407, 1989) designed a tensiometer having an air-pocket at the top of a water-filled tube connected to a porous tip. He used only one tube wherein the water level was required to be above the surface of the ground. His system is limited to measurement depths of 2 to 5 meters and measurements cannot be made remotely.

T. Tokunaga (Soil Science, 54(3):171–183, 1992) attempted measure the water level above a ceramic cup containing an air space. The water level is evaluated using measurements of the air pocket volume. Tokunaga performs calculations using Boyles Law to adjust for the water level below the ground surface. His apparatus is limited to manual measurements because the same tube is used for both water and air feed.

Problems with tensiometers designed for measuring water in the vadose zone include, uncontrolled water-level changes when water from the soil enters the tensiometer, and loss of isolation of the lower cell air volume during drying cycles. Thus, for currently available tensiometer systems to function properly, the maximum installation depth is limited to 5–7 meters. None of the currently available tensiometer systems are conducive to remote operation.

SUMMARY OF THE INVENTION

It is an object of this invention provide a tensiometer capable of measuring liquid pressure in a liquid-containing material surrounding the tensiometer by measurement of a single parameter, the pressure of an isolated volume of air in the tensiometer. It is a further object of the present inventive tensiometer to measure water pressure in the soils of the vadose zone or groundwater aquifer by measurement of that single parameter. It is a another object of the invention to measure water pressure in surrounding soil when the water pressure is increasing with time and when it is decreasing with time. It is yet an additional object of the invention to measure the water tension of soil remotely, and using automated data acquisition instrumentation.

The inventive tensiometer comprises a chamber having an upper cell and a lower cell. The upper cell has at least two feed tubes directly connected to it, one for gas flow and one for liquid flow. A volume of air or other gas resides in the lower cell and this gas-volume is isolated from the upper cell. The gas-volume is in contact with a column of liquid in the lower cell, which, in turn, is in contact with the liquid surrounding the tensiometer, i.e. the liquid pressure to be measured. As the pressure of the surrounding fluid changes, the lower-cell column of water rises or drops slightly so that the lower-cell gas-volume expands or contracts proportionally to changes in the liquid column height. Thus changes in the pressure of the isolated gas volume in the lower cell indicate the degree of saturation of and pressure of the surrounding liquid.

SUMMARY DESCRIPTION OF THE DRAWINGS

FIG. 1: shows a schematic representation of one embodiment of the inventive tensiometer.

FIG. 2: shows a schematic representation emphasizing the space where the lower-cell air volume is confined.

FIG. 3: shows a family of curves indicating the change in height of the lower-cell water column for a particular set of conditions.

FIG. 4: shows a laboratory setup used for tensiometer testing.

FIG. 5: shows the change in lower-cell air pressure, and water level changes in the upper and lower cells as a result of applied pressure to the surrounding liquid.

FIG. 6: shows test response of air pressure in upper and lower cells as the pressure applied to surrounding water increases.

FIG. 7: shows data taken at a field test site.

FIG. 8: shows a fabrication layout for the tensiometer used in tests at about 35 meters below the surface of the ground.

DETAILED DESCRIPTION OF THE INVENTION

The inventive tensiometer comprises, a) a chamber having an upper and lower cell, b) a column of liquid in the lower cell having an essentially constant height; c) a volume of gas in the lower cell that is isolated from gas in the upper cell and from gas outside the tensiometer; d) an air pressure sensor in contact with the isolated volume of gas; e) a volume of liquid in the upper cell, in contact with the liquid volume in the lower cell; f) a porous section on the lower cell through which liquid can pass, and g) at least one air feed tube and one water feed tube connected to the chamber.

Definitions:

Use of the term "surrounding material" herein means material surrounding the porous section of the tensiometer.

Use of the term "surrounding soil" herein means soil surrounding the porous section of the tensiometer.

Use of the term "surrounding liquid" herein means liquid in the material surrounding the porous section of the tensiometer.

Use of the term "surrounding water" herein means water in the material or soil surrounding the porous section of the tensiometer.

Use of the term "upper-cell liquid" herein means liquid in the upper cell of the tensiometer.

Use of the term "upper-cell water" herein means water in the upper cell of the tensiometer.

Use of the term "lower-cell liquid" herein means liquid in the lower cell of the tensiometer.

Use of the term "lower-cell water" herein means water in the lower cell of the tensiometer.

Use of the term "lower-cell gas" herein means gas in the lower cell of the tensiometer.

Use of the term "lower-cell air" herein means air in the lower cell of the tensiometer.

Use of the term "upper-cell gas" herein means gas in the upper cell of the tensiometer.

Use of the term "upper-cell air" herein means air in the upper cell of the tensiometer.

The chamber of the tensiometer has an upper and a lower cell. The lower cell maintains an essentially constant liquid level and a trapped air volume that is isolated from the upper cell. Depending upon the embodiment used, the liquid level in the upper cell may vary or may remain relatively constant with the saturation level of liquid in the material surrounding the porous section of the lower cell. Because the air volume in the lower cell is isolated and because the lower liquid height is kept essentially constant and is in equilibrium with the surrounding liquid, the pressure of the isolated lower air volume is directly proportional to the pressure of the surrounding liquid. In turn, the pressure of the surrounding liquid is proportional to its saturation.

Figure 1:
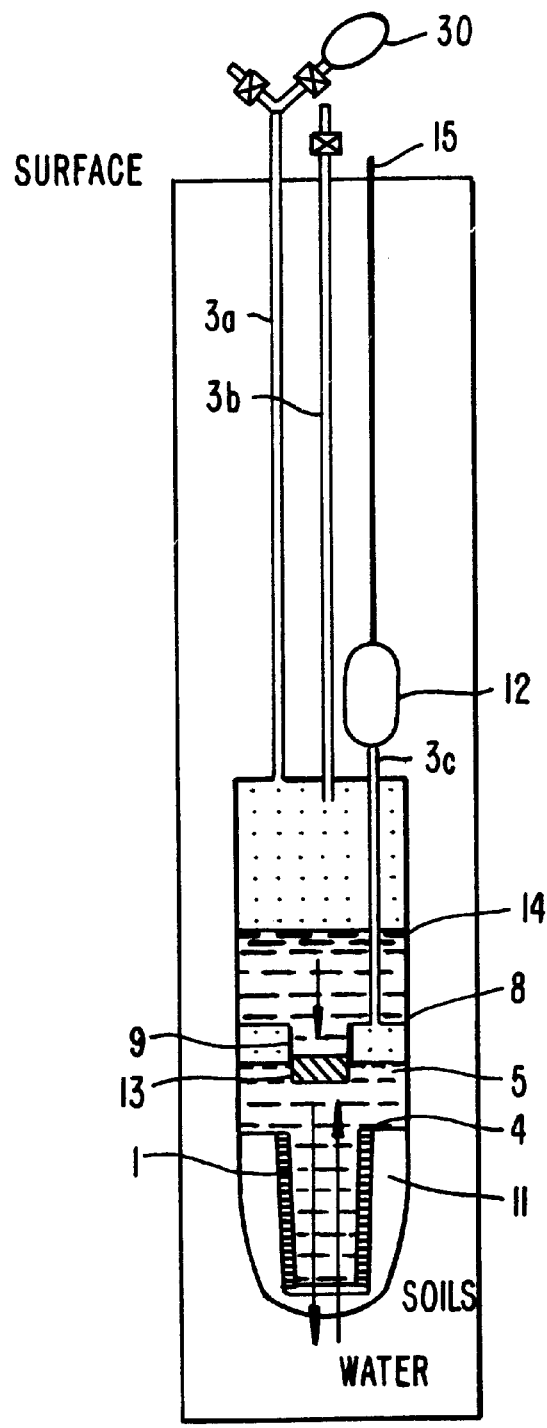

FIG. 1 shows a schematic of the inventive tensiometer. Separator 8 divides the chamber into a lower cell 6 and an upper cell 7. An opening in the separator, marked in the figure by a flow arrow, allows liquid to enter the upper cell from the lower cell. A connector 9 provides a pathway for liquid to pass from one cell to the other cell. In some embodiments, the liquid flows from the lower to the upper cell and from the upper to the lower cell. In other embodiments a check valve prevents the liquid from flowing from the lower cell to the upper cell. The liquid in the upper cell is essentially a reservoir that allows the lower liquid height to remain essentially constant. When the saturation of the surrounding material 20 increases, liquid flows into the lower cell 6. When the saturation of the surrounding material decreases, liquid flows out of the lower cell 6 into the surrounding material.

The interior wall of the tensiometer 16, the separator 8, and the connector 9, form a closed confined space in the lower cell in which an isolated lower-cell gas volume 18 resides. The lower gas volume is in contact with a gas pressure sensor 12. The pressure sensor may be located in the lower gas volume 18 or it may be located near the lower gas volume and connected by a gas-tube 3C. Pressure sensor 12 is connected to electrical read-out connection 15.

When check valve, 13 is used, liquid only flows in one direction, from the upper cell to the lower cell. When the surrounding material increases in saturation, liquid flows into the lower cell of the tensiometer. The incoming liquid causes the lower-cell liquid level 5 to rise slightly and to compress the lower-cell gas.

In contrast, when the surrounding material decreases in saturation, or dries, liquid flows out of the lower cell into the surrounding material. It is necessary to prevent the lower liquid-cell level from dropping below the level of connector 9, so that the approximate water level is always known. To prevent the lower-cell liquid level from dropping below the level of connector 9 during a drying spell, liquid flows from the upper cell into the lower cell through connector 9 and check valve 13 to replace liquid lost to one lower cell during the drying cycle.

A "Y" connector is attached to tube 3A. One of the branches of the Y is connected to the pressure sensor 30 to measure the upper cell gas pressure $P_u$. Each branch of the Y connector has a turn-off valve. The pressure sensor is connected to one branch during water replenishment. It may remain connected or be disconnected when water is not being replenished. A reservoir of liquid (not shown) is connected to the other branch. The connection between the upper-cell gas and the pressure sensor 30 is turned off when tube 3A is used to replace liquid lost to the upper cell. Conversely, the connection to the liquid reservoir was turned off when the upper-cell gas pressure was being measured. Tube 3B has a turn-off valve at the top end and during venting the valve is opened. Optionally a suction device (not shown) is attached to the top of tube 3B. For manual operation, the suction device is operated directly through the turn-off valve. Alternatively, for remote operation, the suction device can be connected through a "Y" connector having a turn-off valve on each branch. When tube 3B is used as a vent, the turn-off valve to the suction mechanism is turned off and the other branch is opened. When a suction was pulled through 3B, the valve is closed on branch of the Y connector used to vent. Usually during operation of the tensiometer, both tube 3A and 3B are sealed. In order to determine the presence of water in the upper cell, $P_u$ was compared to the lower-cell gas pressure, $P_l$, and when $P_u$–$P_l$ is less than or equal to approximately 1 cm of pressure (expressed in cm of water), pressure sensor 30 is temporarily bypassed and liquid is added to the upper cell. Preferably the liquid is added through tube 3A and vented through tube 3B, which is installed having one end about 1 cm lower into the upper cell than tube 3A. Optionally suction is applied to tube 3B to help pull liquid into the upper cell. If the liquid entering through tube 3A overfilled, it is removed by suction through 3B. Removal of excess liquid in this manner preserved an air pocket, having a height approximately equal to the amount of inset of tube 3B, in the upper cell. Additionally, the suction helps to clear tube 3A of any residual liquid droplets.

A manual pressure meter can be substituted in some circumstances for air pressure sensor 30. This might be desirable when the tensiometer is not operated remotely or in order to minimize manufacturing costs.

The inventive tensiometer can be operated independently of a suction device. As depth of the tensiometer installation increases, the suction element becomes more important to operation. Preferably a suction device is used for installations lower than 5 meters. Even more preferably a suction device is used for installations below 3 meters.

The inventive tensiometer can also be operated by adding liquid through either tube 3A or tube 3B. Similarly, pressure sensor 30 can be attached to either tube and neither tube must have the inset into the upper cell in order to work.

Further, tube 3B may be extended to the bottom of the lower cell liquid for sampling the surrounding liquid that has entered the lower cell. Alternatively, a forth tube is used for this function.

Following the line of reasoning described by W. A. Jury, et al. (1991), *Soil Physics* (John Wiley & Sons, N.Y.), pages 52–60, the pressure of the water, or other liquid, in the surrounding material is calculated by, $$P_{surrounding\ liquid} = P_{lower\text{-}cell\ air} + P_{lower\text{-}cell\ water} \quad (1)$$

where $P_{lower\text{-}cell\ air}$ is the pressure measured using air pressure sensor 12 (expressed in water head units, such as cm), and $P_{lower\text{-}cell\ water}$ is the pressure of the water column in the lower cell, which is relatively constant due to the inventive tensiometer design, and varies only slightly compared to the change in lower-cell gas pressure. When $P_{lower\text{-}cell\ water}$ is expressed in water head units, $P_{lower\text{-}cell\ water}$ equals the distance between the bottom of the connector 9 and the center of the porous tip (see Jury, referenced above).

Most frequently the porous section on the lower cell is in the form of a porous tip. FIG. 1 shows the porous section in the form of a tip 1. The porous section or tip is designed to provide good contact between the tip and surrounding material in which liquid saturation is to be measured. In one important application of the inventive tensiometer, the material is soil and the liquid is water. The tip can have a cylindrical shape, or a conical shape, or any other shape that enhances contact with the soil in a particular geological setting or facilitates manufacture. For example, the upper portion of the tip may be cylindrical and the lower portion conical. The cylindrical portion of the porous tip maximizes surface contact with soil while the conical shape may penetrate some soils better than the cylindrical shape. The cylindrical shape has been found advantageous in soft material, such as soil-slurry, silica flower, or fine sand. The porous tip may be made from any material that allows water to flow through it but does not plug up easily. Both ceramic material and stainless steel porous tubes have been used to make the inventive tensiometer. Other materials or combinations of materials that can be used to construct the porous tip will be apparent to those of ordinary skill in the art. Stainless construction of the porous tip is particularly useful when liquids such as volatile organic compounds are to be measured. In one embodiment, the porous tip was made from ceramic material obtained from SoilMoisture Inc. located in Santa Barbara, Calif. In another embodiment, the porous tip was made from a porous stainless-steel tube obtained from Soil Measurement Systems Inc., located in Tucson, Ariz.

The porous section or tip is connected to the lower cell using an air tight coupling. The coupling comprises any of the generally available connecting means typically known to mechanical engineers and technicians of ordinary skill in the art. For example, silastic, welding, or soldering was used in construction of the prototypes described in examples below.

In some circumstances, hydraulic connectivity between the material in which liquid saturation is to be measured and the interior of the porous tip is enhanced by surrounding the tip with a backfill material 11. This can take the simple form of attaching a porous bag filled with soils taken during drilling the site for installation or fine sand around the tip. Other materials can also be used, as will be apparent to those of ordinary skill in this field. For laboratory tests described below, a fine material backfill element 11 was not used. It is used primarily in field conditions.

The inventive tensiometer is used to measure water pressure where the surrounding material comprises soil. In that case, the liquid is water and the gas is most likely air. Both the water and air may be mixed with impurities such as volatile organic compounds (VOCs).

By using electronic instrumentation to measure the lower-cell air pressure, water saturation can be measured remotely through both wetting and drying cycles. Water replacement in the upper cell can be performed either by instrumentation or manually when necessary. Depending on the soil saturation this interval between supplementing the water in the upper cell can vary from about once a month to about once a year. For example, in one case the interval could be 2 months and in a another 3, 4, 5 7 9 or 11 months. A data acquisition system is connected to pressure sensors 12 and 30, and optionally to the liquid reservoir if the liquid replacement is to be controlled automatically. The data acquisition system can be interfaced to a system controlling irrigation of the surrounding material or soil.

Two easily apparent applications of the present soil water monitoring device are 1) agriculture, and 2) landscaping and gardening.

The inventive tensiometer is used in boreholes to measure water pressure of soils and rocks. Several tensiometers can be installed at different depths along a single borehole, or each tensiometer can be installed in an individual borehole above and below the ground water table. In that way water flux can be measured.

The inventive tensiometer is useful in both vertical and slanted boreholes.

Further, the present inventive tensiometer is installed in liquid storage tanks, canals and lakes in order to remotely measure the water level and its fluctuations, Water or liquid samples can be taken if tube 3B is extended to the bottom of the lower cell water or if a fourth tube is used.

Figure 2:
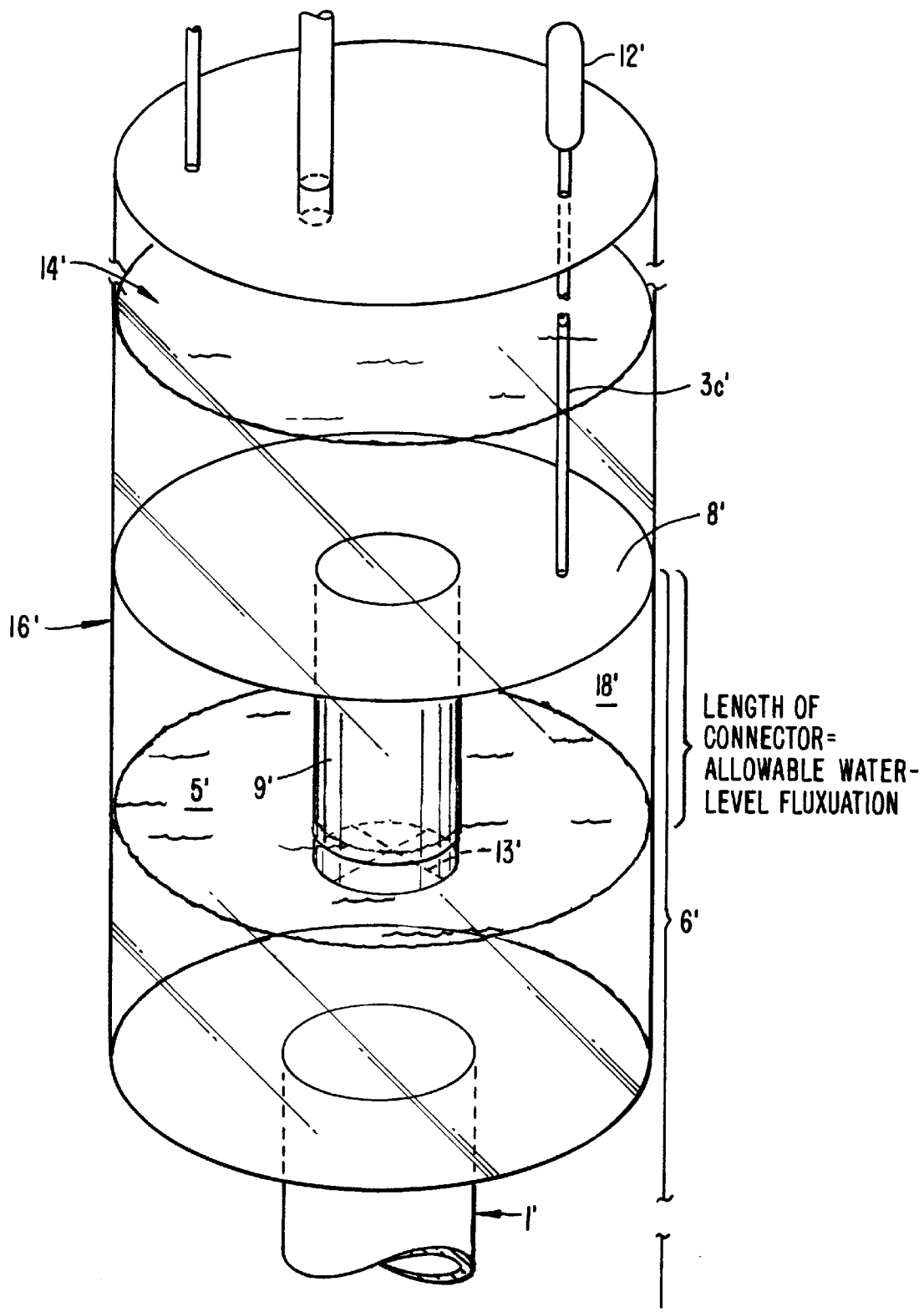

FIG. 2 shows an enlarged partial view of lower cell 6', specifically showing and the space in which the lower-cell gas volume 18' is confined. The geometry of this confining space is important. The height to width ratio of confining space 18' is very important. The maximum height of the confining space is determined by the length of connector 9' that extends into the lower cell. The confining space is bounded by the portion of connector 9' that extends into the lower cell, the inner wall of the tensiometer chamber 16', the separator 8' that divides the upper and lower cells, and the top surface of the lower-cell water. When the lower-cell water level rises, the confining space shrinks, compressing the lower-cell air, and increasing its pressure, which is measured using a pressure sensor 12' in contact with the confined lower-cell air. The pressure sensor may be located in the confined space, or it may be placed near space 18', connected by an air tube having as small a diameter as possible. The air volume in the connecting tube should be small with respect to the volume of space 18'. Preferably the air volume in the connecting tube is less than about 15% of the volume of the confined space in the lower cell. Even more preferably the air volume in the connecting tube is less than about 10% of the volume of the confined space in the lower cell. Most preferably the volume of air in a connecting tube is kept to zero because the sensor is placed inside the region 18'. Another highly preferred configuration is to locate the pressure sensor immediately outside the upper-cell tensiometer casing as illustrated in FIG. 1. This may be most preferable from a manufacturing point of view. As the connector between the air-pressure sensor and the air volume 18' increases, response time slows and sensitivity is lost. With the sensor located as illustrated in FIG. 1, changes in water-pressure in the surrounding soils as small as about 0.5 mbar to about 1.0 mbar can be measured. Of course larger changes can also be measured. A great benefit of the present invention however is in its increased measurement sensitivity.

During periods of excessive drying, gas from the surrounding soil may diffuse into the lower cell through the porous section. That gas then may alter the volume of gas in the lower cell. As long as the volume of diffused gas is not large enough to cause the lower cell liquid to drop below the bottom of the connector 9, equilibrium will reestablish by itself. If the lower cell water drops below the level of connector 9, water from the upper cell flows into the lower cell, and reestablishes the water level in the lower cell just above the bottom of connector 9. Connecting the data acquisition system to an automatic irrigation device will help prevent this from happening by limiting the extent of the soil drying cycle.

The height to width ratio of the lower-cell air volume 18' is governed by the following considerations: 1) The height must be great enough that as the surrounding soil increases its water pressure, and water enters the lower cell, the water column in the lower cell does not rise more than the height of the confining space (note that for the configuration shown in FIG. 1, the maximum height of the lower-cell-gas-confining space is the height of the connector 9); and 2) The width (or diameter) must be great enough that the change in the lower-cell water level, $h_w$, is small with respect to the total column height of the lower-cell water.

The tensiometer chamber can take many shapes. It can have a rectangular, ellipsoidal, circular, conical or other cross-section, for example.

The tensiometer can be manufactured out of any of the standard materials known to those of ordinary skill in the art.

Knowing an approximate rate of change of pressure, appropriate dimensions are determined by making calculations of the type, $P_{air-1} V_{air-1} = P_{air-2} V_{air-2}$. P and V refer to the absolute air pressure and volume of the lower cell air, including the air in tube 3C. The indices '1' and '2' indicate values for states 1 and 2.

Assuming a circular cross-sections as shown in FIG. 1, the change in absolute pressure of the lower-cell air from $P_1$ to $P_2$ will the change the height of the lower-cell water, $h_w$, according to the formula, $$\Delta h_w = \frac{[(P_1/P_2) - 1][(D_{lower-cell}^2 - D_{con}^2)h_{con} + D_{tube}^2 L_{tube}]}{(D_{lower-cell}^2 - D_{con}^2)} \quad (2)$$

where,
$P_1$=initial absolute pressure of lower-cell air;
$P_2$=final absolute pressure of lower-cell air;
$D_{lower-cell}$=inner diameter of the lower cell;
$D_{con}$=outer diameter of connector 9;
$D_{tube}$=inner diameter of tube 3C;
$h_{con}$=length of connector 9; and
$L_{tube}$=length of tube 3C.

In order to prevent lower-cell water from entering tube 3C, $\Delta h_w$ must be smaller than $h_{con}$. This is the key design element of the inventive tensiometer.

Figure 3:
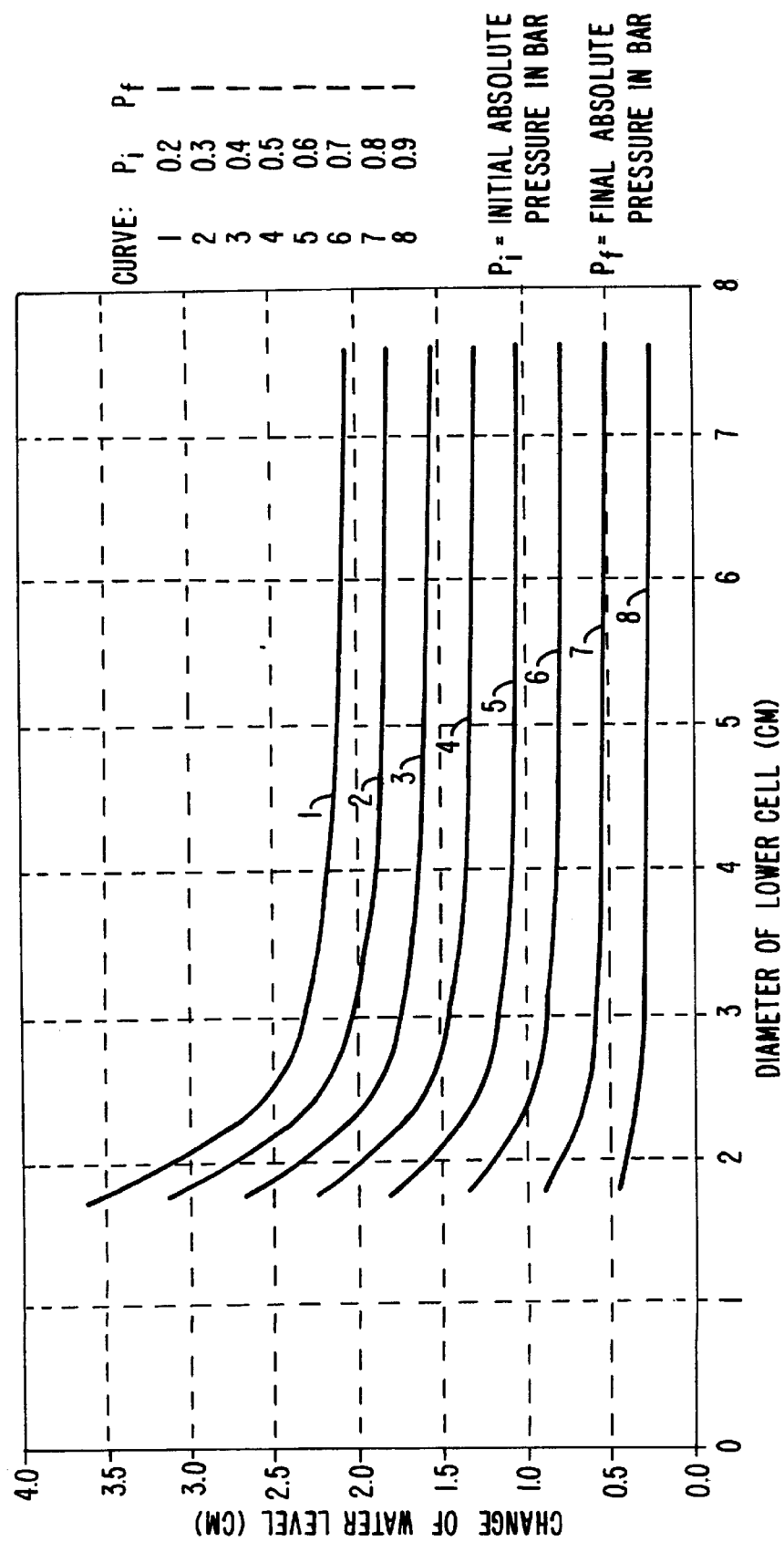

FIG. 3 shows a family of curves calculated using equation (2). The diameter of the connector was assumed to be 1.25 cm. The top curve shows the change of lower-cell water level for a pressure change in the lower-cell air starting at 0.2 bar and ending at 1 bar. Sequential curves are for initial absolute pressures of 0.3, 0.4, 0.5, 0.6, 0.7, 0.8, and 0.9 bar. All the final pressures used were 1.0 bar. The change in height for the lower-cell water column as a result of changes in lower-cell air pressure, caused by a change in the pressure of the surrounding water, was calculated using the above formula.

Several tensiometer prototypes were constructed having geometries that satisfy the above conditions. Some examples are:

| Prototype | 1 | 2 | 3 |
|---|---|---|---|
| chamber inside diameter (cm) | 4.45 | 2.3 | 4.0 |
| upper cell height (cm) | 20 | 34.3 | 28 |
| lower cell height (cm) | 5.6 | 4.1 | 4.0 |
| tube 3C length (cm) (typically a few cm longer than upper-cell height) | ~23 | ~36 | ~31 |
| connector 9 height (cm) | 1.9 | 2.5 | 1.9 |
| connector 9 outside diameter (cm) | 1.25 | 0.9 | 1.25 |
| porous tip length (cm) | 5 | 7.9 | 5.2 |
| porous tip diameter (cm) | 2.2 | 2.3 | 4.5 |

Prototype 1 was made from transparent acrylic tubing. The parts were joined by epoxy. This prototype was used for laboratory testing Prototype 2 was made from stainless steel and parts were joined by welding and soldering; swage locks were used to connect tubes to the chamber. This prototype was used for taking measurements at McClellan Air Force Base.

Prototype 3 was made from PVC plumbing parts that were joined using a special PVC type glue and epoxy. It was used for testing at Box Canyon, Id.

It can be seen from this list of prototypes that a variety of dimensions satisfy the criteria for satisfactory operation in different situations. Fundamentally, the volume of the confined gas space in the lower cell and the height of the lower cell water column must accommodate the expected range of external water pressures to be measured.

Figure 4:
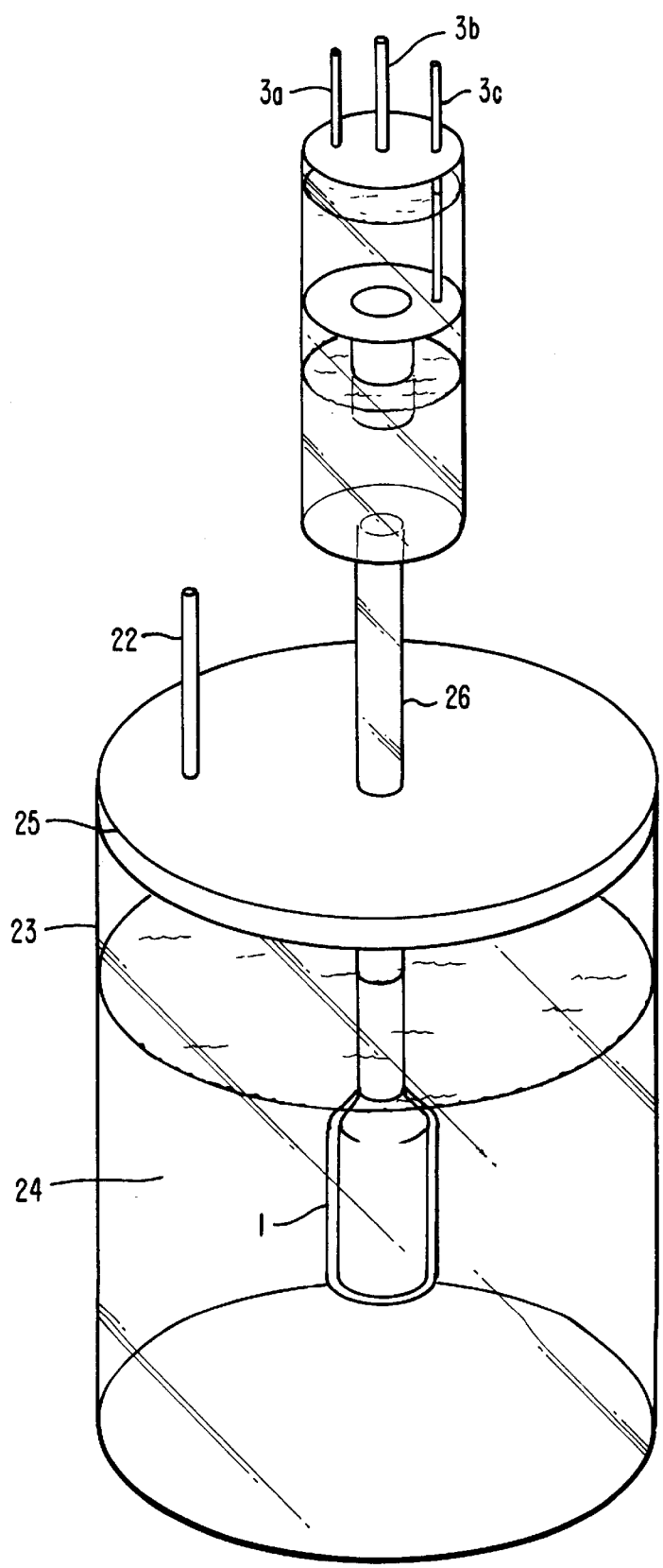

FIG. 4 shows a tensiometer set-up that was used for laboratory testing (Prototype 1). Pressure is applied through port 22 of jar 23. Jar 23 is partially filled with water 24 and sealed at the top 25. A porous section 1 is connected to the lower-cell of the tensiometer by tube 26. In this apparatus the porous tip was connected to the lower cell by a tube that was 26 cm long.

EXAMPLE 1

Using equation (1) and FIG. 3, the effect of changes in the height of the lower-cell liquid column on measuring pressure changes in the surrounding liquid can be determined for various diameters of the lower cell. This figure assumes a constant value for the outer diameter of connector 9 of 1.25 cm.

FIG. 3 shows a family of curves illustrating changes in lower cell water height as a function of pressure change in the lower-cell air pressure. The final pressure was always 1 bar (1 bar=1019.7 cm water). The initial pressure was 0.2 bar for the top curve, 0.3 bar for the next curve and so on. The bottom curve had an initial pressure of 0.9 bar and a final pressure of 1 bar. The x axis shows the diameter of the lower cell and the y axis gives the corresponding change in lower-cell water height. It can be seen that for larger diameters the water height changes less.

The top and bottom curves, that is the extremes, will be used below to calculate the effect of the change in lower-cell water level on surrounding pressure using Equation 1.

For a pressure change from 0.2 bar to 1 bar, and a lower cell diameter of 1.8 cm, the change in lower cell water level is seen from the graph to be 3.6 cm.

Equation 1 states, $$P_s = P_{l\text{-}c\ air} + P_{l\text{-}c\ water}$$

or, $$P_{l\text{-}c\ air} = P_{l\text{-}c\ water} - P_s$$

where $P_s$ is the pressure of the surrounding water;
$P_{l\text{-}c\ air}$ is the measured pressure of the lower-cell air;
$P_{l\text{-}c\ water}$ is the pressure of the lower-cell water.

For purposes of this calculation,
all pressures are absolute pressures, expressed in cm of water.
A subscript "i" indicates an initial value and a subscript "f" indicates a final value.
The lower cell diameter is held at 1.8 cm.
The initial lower-cell water height of 5 cm is used (i.e. $P_{l\text{-}c\ water\ i}$=5 cm water).

Now, consider the circumstance of greatest pressure change, the top curve, where the lower-cell air pressure changes from 203.94 cm water (0.2 bar) to 1019.7 cm water (1 bar). Reading the water height off the ordinate, it can be seen that the corresponding change in lower-cell water level is 3.6 cm water. That is $P_{l\text{-}c\ water\ i}$=5 cm and $P_{l\text{-}c\ water\ f}$=8.6 cm. In tabular form:

| | | | | | |
|---|---|---|---|---|---|
| $P_{1\text{-}c\ air\ i}$ | 203.94; | $P_{1\text{-}c\ air\ f}$ | 1019.7; | $\Delta P =$ | 815.76 |
| $P_{1\text{-}c\ water\ i}$ | 5.0; | $P_{1\text{-}c\ water\ f}$ | 8.6; | $\Delta P =$ | 3.6 |
| $P_{s\ I}$ (sum) | 208.94; | $P_{s\ f}$ (sum) | 1028.3; | $\Delta P =$ | 819.36 |

All pressure values given in water pressure-head units of cm water. It can be clearly seen that the influence of changes in height of the tensiometer water column, $P_{l\text{-}c\ water}$, is negligible. The lower-cell water column would change in height even less if a larger diameter was chosen for the lower cell, as can be seen from the shape of the curves in FIG. 3.

In contrast, for the bottom curve, the lower-cell air pressure changes from 917.73 cm water (0.9 bar) to 1019.7 cm water (1 bar). $P_{l\text{-}c\ water\ i}$=5 cm and $P_{l\text{-}c\ water\ f}$=5.4 cm. In tabular form:

| | | | | | |
|---|---|---|---|---|---|
| $P_{1\text{-}c\ air\ i}$ | 917.73; | $P_{1\text{-}c\ air\ f}$ | 1019.7; | $\Delta P =$ | 101.97 |
| $P_{1\text{-}c\ water\ i}$ | 5.0; | $P_{1\text{-}c\ water\ f}$ | 5.4; | $\Delta P =$ | 0.4 |
| $P_{s\ I}$ (sum) | 922.73; | $P_{s\ f}$ (sum) | 1025.1; | $\Delta P =$ | 102.37 |

The negligible effect of the tensiometer water column on the correlation between the measured lower-cell air pressure and the surrounding water pressure is again readily apparent.

These values are well within the required accuracy of pressure measurements in the subsurface.

EXAMPLE 2

Figure 5:
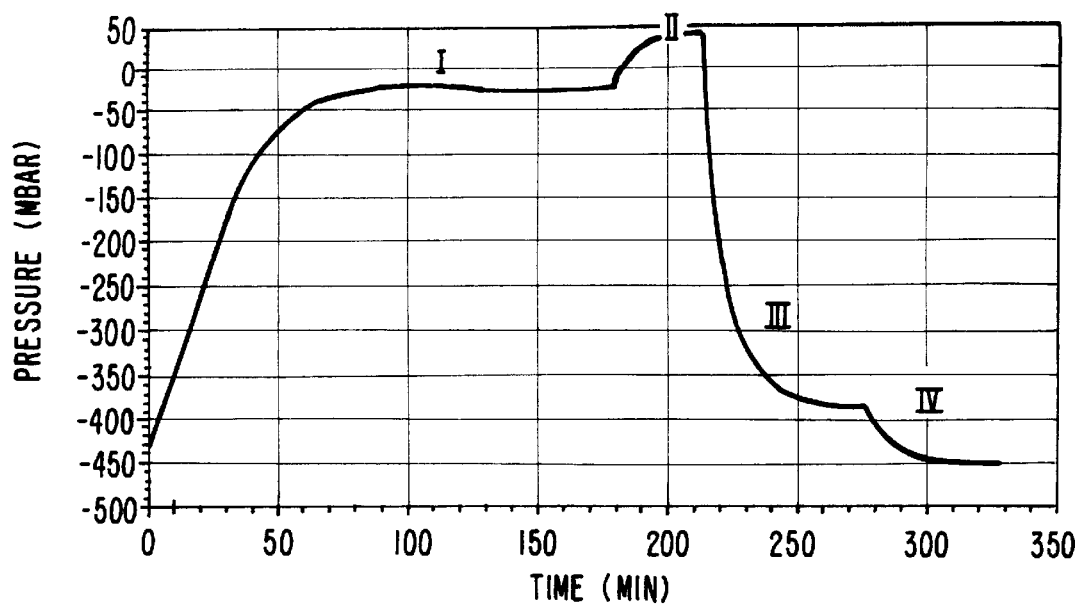
Figure 5:
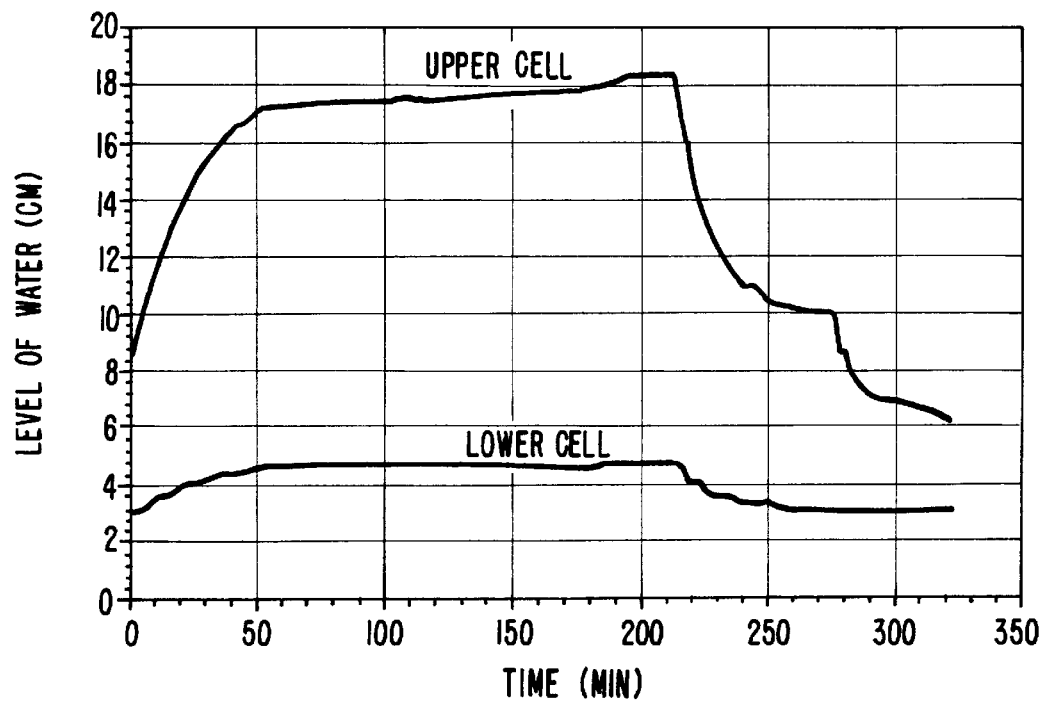

Using the laboratory test apparatus shown in FIG. 4, lower-cell air pressure and water level changes in both the upper and lower cells of the tensiometer were measured as pressure was applied through port 22 to the surrounding water. The tensiometer was fabricated from acrylic tubing and fabricated according to the dimensions of prototype 1. Tubes 3A and 3B were each three meters long. The pressure was applied in four steps, denoted as I, II, III, and IV. For step I the pressure was brought to 0 mbar; for step II the pressure was brought to +70 mbar; for step III the pressure was brought to −360 mbar; and for step IV the pressure was brought to −423 mbar. FIG. 5 shows the results.

The top panel shows the changes in lower-cell air pressure during each of the four steps, noted as I, II, III, and IV. The lower-cell air pressure was measured using an electronic pressure transducer, "Tensimeter (TM)", manufactured by Soil Measurement Systems (266 N. Oracle Rd., Tucson, Ariz.) for pressure sensor 12. (The same type of pressure sensor can be used for 30, shown in FIG. 2, to measure the upper-cell air pressure.) The read-out was digital and recorded manually, but could have been interfaced to a computer or controller as well. The lower panel of FIG. 5 shows that when an initial pressure of −433 mbar increased up to 42 mbar, the water level in the lower cell changed only 1.6 cm, in contrast to a change of 10 cm in the upper-cell water level.

The changes in water level were measured using a linear measure placed immediately outside the test chamber which was manufactured from transparent acrylic tubing. Changes in air pressure were measured using a standard laboratory pressure sensor at the end of tube 3C.

EXAMPLE 3

Figure 6:
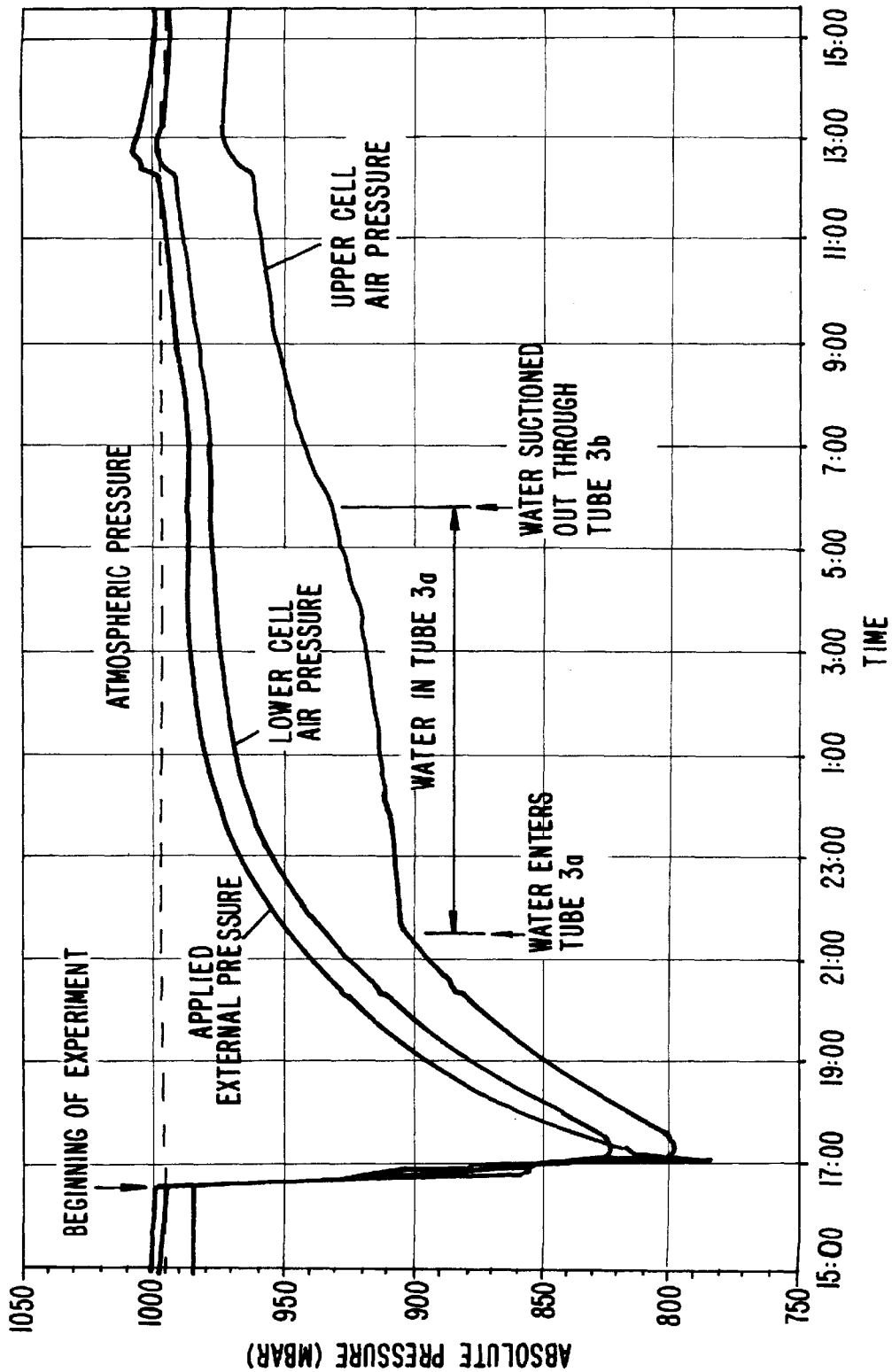

The tensiometer configured with an air pressure sensor 12 placed outside the upper cell as shown in FIG. 1, was tested in the same way as described in Example 2. The absolute air pressure measurements were made using a ParoScientific, Inc. pressure sensor (model # 8DP130-I) for pressure sensor 12 and 30. The length of access tubes 3A and 3B was three meters. The porous portion of the lower cell was made of porous stainless steel tubing having an inside diameter of 1 inch. The upper and lower cells were connected to a PC-based data acquisition system operated by a commercially available, PC-based, LabView (TM) program. Air pressure sensors 12 and 30 were read out by the data acquisition program. There are many such programs available for use, or the practitioner of the invention can easily write program steps to read out this information. Measurements were made every five minutes. The time response curve of the pressure measured in the lower cell essentially matched the applied pressure curve. During the transient period of increasing pressure, when the upper-cell water level did not reach the top of the upper cell, the air pressure curve measured with sensor 12 was smooth. When the water level reached the top of the upper cell, water entered the tube 3A, and the upper-cell pressure-time curve measured with sensor 30, became rough, however the air pressure measured by sensor 12 remained smoothly constant. This is shown in FIG. 6. When excess water was removed from tube 3A by applying a suction to tube 3B and the pressure-time curve for the upper cell became smooth again. Thus, measurements of the air pressure in the lower cell, on a buried tensiometer, were unaffected by changes in the upper cell pressures.

The difference between the pressure measured in the lower cell and applied pressure varied in a very narrow range from about 1.07 cm to about 1.65 cm, reflecting very small changes in the lower cell water level. It is also apparent from FIG. 6 that the time response of the inventive tensiometer is relatively small, less than about one hour.

EXAMPLE 4

Tensiometer response time in soils was tested by adjusting the applied pressure manually. A tensiometer having 10 meter long access tubes 3A and 3B was buried in soils infilling the fracture in basalt rocks at a Box Canyon Site in Idaho. Pressures and water levels were measured in both the upper and lower cells. The water pressure head in the surrounding soils was calculated for both the upper and lower cells as described above. They became practically equal 2 hours after installation. The gas pressure in the upper cell was adjusted to minimize any time variation of pressure within 2 hour periods, thereby minimizing water exchange between the tensiometer and soils. In that way the response time of the tensiometer was reduced.

EXAMPLE 5

Figure 7:
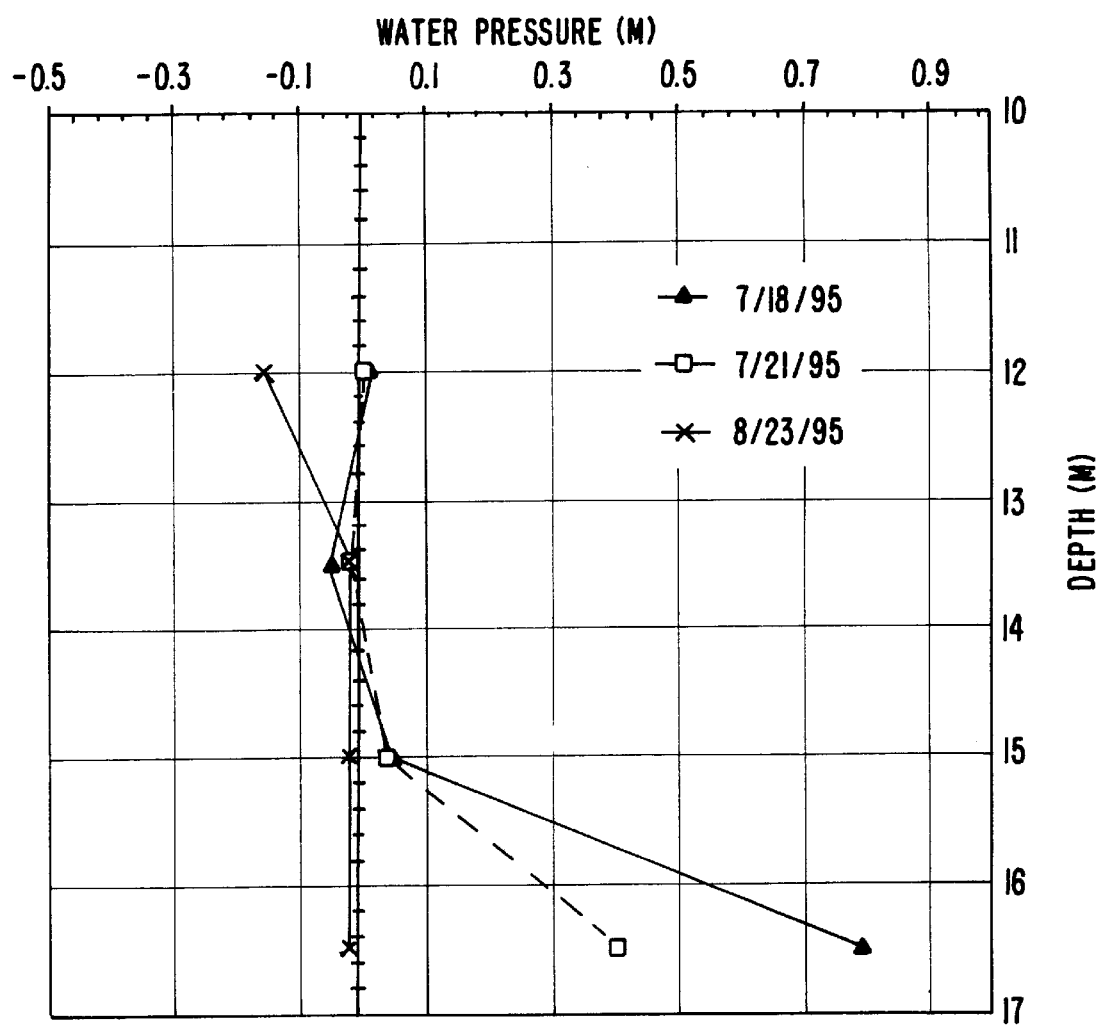

Four tensiometers made according to prototype 3 were installed in a borehole at a Box Canyon field test site in Idaho. They were installed at depths of 12.2, 13.7, 15.2, and 16.8 meters in order to take measurements of the water pressure in the unsaturated and saturated rocks in the vicinity of the water table. FIG. 7 shows one a sample set of data. The water pressure scale is shown across the top of the graph. A water pressure reading of zero indicates the upper level of the water table. Positive water pressure values are below the water table and negative values are above it. The depth at which a data point is taken is shown on the right side of the graph.

Data is shown for three days. Jul. 18, 1996 is indicated with a triangle; Jul. 21, 1996 is indicated with a square; and Aug. 23, 1996 is indicated with an "X".

The zero values for water pressure (which indicate the depth of the water table) are shown at between about 14.3 meters and 14.7 meters. This is consistent with direct water level measurements in the same borehole.

The measurements taken at 16.8 meters on 7/18 (triangle), 7/21 (square), and 8/23 ("X") clearly show the water table level dropping over the measurement period. The overall data shows progressive drying over the period.

EXAMPLE 6

Figure 8:
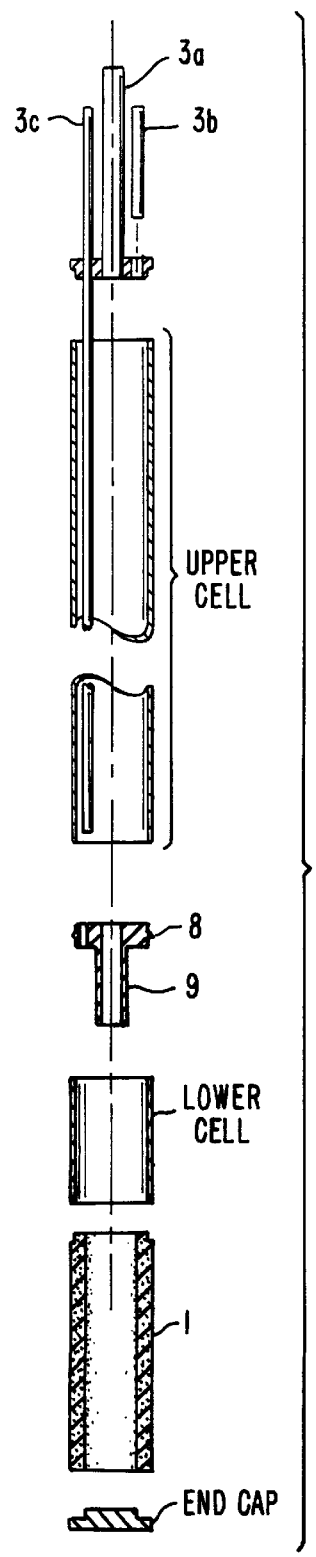

Prototype 2 was manufactured for installation at McClellan Air Force Base. It had a smaller chamber diameter than previously constructed tensiometers in order to accommodate a particularly small available space in the borehole because of the presence of several other probes in the same borehole. Thirteen tensiometers were placed in each of two boreholes. The deepest was placed at 34.5 meters below the earth surface. The tensiometer chamber was made from type 304 stainless steel. The porous tip was made from porous stainless steel tubing, 0.905 to 0.935 cm in diameter. A tensiometer fabrication layout is shown in FIG. 8.

Data collection is in progress at this writing. All tensiometers are performing to expectation.

Having thus described the invention, I claim:

1. A tensiometer for measuring liquid pressure comprising,
   a) a housing defining a chamber having an upper and a lower cell;
   b) a column of liquid in the lower cell having a height that does not vary more than the height of an isolated gas volume located in the lower cell;
   c) a volume of gas in the lower cell that is isolated from gas in the upper cell, and which is in contact with the column of liquid in the lower cell;
   d) an air pressure sensor in contact with the isolated volume of gas in the lower cell;
   e) a volume of liquid in the upper cell that is in contact with the liquid column in the lower cell;
   f) a porous section in the lower cell through which the lower-cell column of liquid contacts the any surrounding liquid; and
   g) at least one gas venting tube and one liquid feed tube connected to the chamber.

2. A tensiometer for measuring water pressure comprising,
   a) a housing defining a chamber having an upper and a lower cell;
   b) a volume of air in the lower cell that is isolated from air in the upper cell, and which is in contact with a column of water in the lower cell;
   c) a column of water in the lower cell having a height that does not vary more than that of the isolated air volume height located in the lower cell;
   d) an air pressure sensor in contact with the isolated volume of air in the lower cell;
   e) a volume of water in the upper cell that is in contact with the water column in the lower cell;
   f) a porous section in the lower cell through which the lower-cell column of water contacts any water that surrounds the tensiometer;
   g) at least one air feed tube having one end terminating in the upper-cell; and
   h) at least one water feed tube having one end terminating in the upper-cell.

3. The apparatus of claim 2 further having a check valve between the upper cell and the lower cell oriented so that water flow between the two cells is limited to flow from the upper cell to the lower cell.

4. The apparatus of claim 2 further comprising a feed tube that extends from the surface to the water in the lower cell.

5. The apparatus of claim 2 further comprising a hydraulically conductive layer of material between the porous section and any surrounding material, wherein the hydraulically conductive layer comprises soil removed from a borehole, sand, or other porous material, that is surrounded by a porous container.

6. The apparatus of claim 2 further comprising an air pressure sensor connected to the water feed tube.

7. The apparatus of claim 2 further comprising a suction device.

8. The apparatus of claim 7 wherein the suction device is connected to the tensiometer's air vent tube.

9. The apparatus of claim 2 further comprising a data acquisition system.

10. The apparatus of claim 9 wherein the data acquisition system is electrically connected to irrigation control instrumentation.

11. The apparatus of claim 2 additionally comprising an air-filled tube connecting the pressure sensor to the isolated column of air in the lower cell.

12. The apparatus of claim 11 wherein the volume of air in the air-filled connecting tube is between about 0.1% and about 15% of the lower-cell air volume.

13. The apparatus of claim 11 wherein the volume of air in the air-filled connecting tube is between about 1% and about 10% of the lower-cell air volume.

14. A tensiometer for remotely measuring water pressure comprising,
   a) a housing defining a chamber divided into an upper and a lower cell by a separator having an opening for fluid exchange between the cells;
   b) a connector attached to the separator at the perimeter of the opening and extending into the lower cell a distance $h_{con}$;
   c) a column of water in the upper cell and supported by the separator;
   d) a volume of air in the upper cell located above the upper-cell water column;
   e) a column of water in the lower cell having a top surface in contact with the outside of the connector and connected to the water in the upper cell through the interior of the connector;
   f) a volume of air in the lower cell residing primarily in a space bounded by the lower cell chamber wall, the connector, the separator, and the top surface of the lower-cell water column;
   g) an air pressure sensor in contact with the lower-cell air;
   h) a porous section in the lower cell;
   i) at least one air feed tube having one end terminating in the upper-cell air volume; and
   j) at least one water feed tube having one end terminating in the upper-cell air volume.

15. The apparatus of claim 14 wherein the connector length, $h_{con}$, is greater than any change in lower-cell water level, $h_w$.

16. The apparatus of claim 14 further having a check valve located in the interior of the connector and oriented so that water only flows from the upper cell to the lower cell.

17. The apparatus of claim 14 further comprising an air tube connecting the air pressure sensor to the lower-cell air.

18. The apparatus of claim 14 further comprising a second air pressure sensor connected to one of the feed tubes.

19. The apparatus of claim 14 further comprising a suction device connected to one of the feed tubes.

20. The apparatus of claim 14 further comprising electronic instrumentation to collect measurement data from the two pressure sensors.

21. An automatic soil irrigation system for wetting soil as a function of its dryness comprising,
   a) a housing defining a chamber divided into an upper and a lower cell by a separator having an opening for fluid exchange between the cells;
   b) a connector attached to the separator at the perimeter of the opening and extending into the lower cell;
   c) a column of water in the upper cell and supported by the separator;
   d) a volume of air in the upper cell located above the upper-cell water column;
   e) a column of water in the lower cell having a top surface in contact with the outside of the connector and connected to the water in the upper cell through the interior of the connector;
   f) a volume of air in the lower cell residing primarily in a space bounded by the lower cell chamber wall, the connector, the separator, and the top surface of the lower-cell water column;
   g) a first air pressure sensor in contact with the lower-cell air;
   h) a second air pressure sensor in contact with the upper-cell air;
   i) a porous section in the lower cell;
   j) at least one air feed tube having one end terminating in the upper-cell air volume; and
   k) at least one water feed tube having one end terminating in the upper-cell air volume;
   l) electronic instrumentation that collects measurement data from the two pressure sensors and delivers the data to an irrigation control system.

22. The apparatus of claim 21 further comprising a water reservoir that is permanently attached to the water feed tube through a Y connection having turn-off valves in each branch.

23. The apparatus of claim 22 wherein the water reservoir connection to the upper cell is controlled remotely.

* * * * *